United States Patent [19]

Kamel et al.

[11] Patent Number: 5,080,924
[45] Date of Patent: Jan. 14, 1992

[54] METHOD OF MAKING BIOCOMPATIBLE, SURFACE MODIFIED MATERIALS

[75] Inventors: Ihab Kamel, Drexel Hill; David B. Soll, Rydal, both of Pa.

[73] Assignees: Drexel University; Ophthalmic Research Corporation, both of Philadelphia, Pa.

[21] Appl. No.: 342,270

[22] Filed: Apr. 24, 1989

[51] Int. Cl.$^5$ .............................................. A61F 2/14
[52] U.S. Cl. ............................... 427/2; 427/40; 427/41; 427/45.1; 427/164; 427/333; 427/412.3; 427/412.4; 427/412.5; 523/105; 623/6
[58] Field of Search ............ 427/2, 40, 41, 162, 427/164, 412.3, 302, 45.1, 333, 412.4, 412.5; 523/105, 106, 112, 113; 623/6, 166; 204/165

[56] References Cited

U.S. PATENT DOCUMENTS

| | | | |
|---|---|---|---|
| 2,999,056 | 9/1961 | Tanner | 522/118 |
| 3,228,741 | 1/1966 | Becker | 351/160 R |
| 3,880,818 | 4/1975 | Shen et al. | 526/322 |
| 3,925,178 | 12/1975 | Gesser et al. | 204/165 |
| 3,944,709 | 3/1976 | Levy | 428/409 |
| 3,959,105 | 5/1976 | Feneberg et al. | 204/165 |
| 3,961,379 | 6/1976 | Highgate | 522/116 |
| 3,985,697 | 10/1976 | Urbach | 523/106 |
| 4,055,378 | 10/1977 | Feneberg et al. | 351/160 R |
| 4,072,769 | 2/1978 | Lidel | 427/38 |
| 4,096,315 | 6/1978 | Kubacki | 428/412 |
| 4,122,942 | 10/1978 | Wolfson | 206/5.1 |
| 4,123,308 | 10/1978 | Nowlin et al. | 427/41 |
| 4,131,691 | 12/1978 | Morley et al. | 427/41 |
| 4,137,365 | 1/1979 | Wydeven et al. | 428/412 |
| 4,143,949 | 3/1979 | Chen | 427/41 |
| 4,189,364 | 2/1980 | Aelion et al. | 522/4 |
| 4,214,014 | 7/1980 | Höfer et al. | 427/40 |
| 4,240,163 | 12/1980 | Galin | 623/6 |
| 4,277,595 | 7/1981 | Deichert et al. | 528/26 |
| 4,312,575 | 1/1982 | Peyman et al. | 351/160 H |
| 4,328,257 | 5/1982 | Muehlberger et al. | 427/34 |
| 4,344,981 | 8/1982 | Imada et al. | 427/40 |
| 4,405,773 | 9/1983 | Loshaek et al. | 526/318.42 |
| 4,409,258 | 10/1983 | Feurer et al. | 427/38 |
| 4,430,458 | 2/1984 | Tighe et al. | 523/108 |
| 4,463,148 | 7/1984 | Höfer et al. | 526/264 |
| 4,478,873 | 10/1984 | Masso et al. | 427/40 |
| 4,656,083 | 4/1987 | Hoffman et al. | 427/41 |
| 4,720,512 | 1/1988 | Hu et al. | 523/112 |
| 4,731,080 | 3/1988 | Galin | 623/6 |
| 4,865,870 | 9/1989 | Hu et al. | 427/2 |
| 4,885,077 | 12/1989 | Karakelle et al. | 427/41 |
| 4,919,659 | 4/1990 | Horbett et al. | 427/2 |
| 4,927,676 | 5/1990 | Williams et al. | 427/2 |

OTHER PUBLICATIONS

H. Yasuda, "Plasma for Modification of Polymers," *J. Macromol. Sci.-Chem.*, A10(3), pp. 383–420 (1976).

Knight et al., "Surface Modification of Intraocular Lenses to Reduce Corneal Endothelial Damage," *AM Intra-Ocular Implant Soc. J*-vol. V, pp. 123–130, Apr. 1979.

Gazard et al., "Lithographic Technique Using Radiation-Induced Grafting of Acrylic Acid into Poly(-Methyl Methacrylate) Films," *Polymer Engineering and Science*, vol. 20, No. 16, pp. 1069–1072 (1980).

K. L. Mittal, "Interfacial Chemistry and Adhesion: Recent Developments and Prospects," *Pure & Appl. Chem.*, vol. 52, pp. 1295–1305 (1980).

Akovali et al., "Polymerization of Hexamethyldisiloxane by Plasma on Activated Charcoal: Investigation of Parameters," *Journal of Applied Polymer Science*, vol. 29, pp. 2617–2625 (1984).

Liu et al., "Polymethyl Methacrylate Resist Sensitivity Enhancement in X-Ray Lithography by In Situ Polymerization," *Appl. Phys. Lett.*, 44(10), pp. 973–975, May 15, 1984.

Keates et al., "Coated Intraocular Lenses," *Ophthalmic Surgery*, vol. 18, No. 9, pp. 693–697 (1987).

*Primary Examiner*—Shrive Beck
*Assistant Examiner*—Terry J. Owens
*Attorney, Agent, or Firm*—Panitch Schwarze Jacobs & Nadel

[57] ABSTRACT

A method of permanently modifying the surface of a substrate material so as to develop a microscopically smooth, biocompatible surface thereon comprises covalently grafting at least a first biocompatible material, preferably having pendant terminal carboxylic acid or amine groups, to the surface of the substrate material by radio frequency plasma-induced grafting. In addition, a method of permanently modifying the surface of the substrate material comprises cross-linking a second biocompatible material to the first biocompatible material grafted to the substrate material using a cross-linking agent. Further, a prosthesis used in mammals, including an intraocular lens, comprises a polymer core and at least a first biocompatible material, preferably having pendant terminal carboxylic acid or amine groups, covalently grafted to the polymer core by radio frequency plasma induction. The prosthesis used in mammals may further comprise a second biocompatible material cross-linked to the grafted first biocompatible material by a cross-linking agent.

23 Claims, No Drawings

5,080,924

METHOD OF MAKING BIOCOMPATIBLE, SURFACE MODIFIED MATERIALS

FIELD OF THE INVENTION

The present invention relates to methods of permanently modifying the surface of materials by plasma-induced and, where desired, post-plasma reactions to produce biocompatible, surface modified materials. In addition, the present invention relates to biocompatible, surface modified prostheses and, in particular, to a biocompatible, surface modified intraocular lens used in mammals.

BACKGROUND OF THE INVENTION

Prosthetic devices or prostheses are commonly used in medical procedures replacing or augmenting defective organs in mammals and humans, in particular, and are numerous and diverse in structure and application. Examples of prostheses include artificial joints, valve replacements, skin grafts, vascular grafts, shunts, plates and contact and intraocular lenses. Typically, prosthetic devices comprise natural and/or synthetic materials which are abrasive on the cellular level Various prostheses in current use or in experimental use comprise metals, ceramics, silicone rubbers, polyesters, polyurethanes and/or polysulfones. Synthetic polymers, such as polymethylmethacrylate (PMMA) and hydroxyethylmethacrylate (HEMA), for example, are preferred polymers for prosthetic use in general and contact lenses and intraocular lenses in particular.

PMMA, for example, has several beneficial characteristics for such prosthetic use, including excellent light transmission, good optical clarity, resistance to fluid diffusion and in vivo deterioration, ease in processing (injection molding or machining, for example) and ease in implantation, such as an intraocular lens, an artificial joint and other implantable prostheses. However, PMMA has several disadvantages in prosthetic use, including hydrophobic properties, a tendency to attach to endothelia, general cellular adhesion and a tendency to become encapsulated with fibrous tissues.

Hydrophobic and/or abrasive prostheses, especially those which are implanted, can cause tissue irritation, edema and scarring. For example, posterior lens capsule opacification is a prevalent problem among those patients who have received intraocular lens implants comprising PMMA and other hydrophobic materials.

It is desirable to modify the surface properties of such hydrophobic and/or abrasive materials without changing the beneficial characteristics thereof, by developing or enhancing surface hydrophilicity, thereby reducing abrasiveness, discouraging tissue adhesion and inhibiting cellular growth, and by developing a smooth surface. Moreover, such surface modification should be resistant to deterioration over time and should have no adverse effects on tissues and cells with which the surface modified material comes in contact.

Those skilled in the art have long recognized the need for biocompatible, surface modified materials for use in prosthetic devices and other materials. For example, U.S. Pat. No. 3,961,379 discloses a bioimplantable device manufactured from a cross-linked, swollen, hydrophilic polymer. These modified polymers must be solid and must be swellable by fluid swelling substances. Once swollen, the solid polymer is polymerized with a modifying substance by, for example, high energy particle radiation.

U.S. Pat. No. 4,189,364 discloses hydrophilic polymers formed in situ by irradiating a mixture of hydroxyalkyl methacrylate and a cross-linking agent. This patent discloses a process for forming hydrophilic polymer articles or hydrophilic polymer coatings on other substrates, such as glass or plastic, by polymerizing a hydrophilic monomer system by high energy particulate irradiation, such as accelerated electrons or nuclear particles including neutrons, protons, alpha, beta and/or gamma particles.

Radiation-induced grafting of acrylic acid onto other polymer films is disclosed by Gazard, M. et al., "Lithographic Technique Using Radiation-Induced Grafting of Acrylic Acid Into Poly(Methyl Methacrylate) Films," *Polymer Engineering and Science*, 20:16 (1980). Gazard et al. disclose that, under ionizing radiation, polymers undergo changes in their properties, especially in their solubility. Ionizing radiation of polymers leads to the formation of free radicals and other intermediates, which may be used to initiate the grafting of a monomer to produce a grafted copolymer with properties different from those of the initial polymer. For example, irradiated PMMA, onto which acrylic acid is grafted produces a graft copolymer which is insoluble in the solvents of PMMA.

U.S. Pat. No. 2,999,056 also discloses that an unsaturated organic acid may be attached to a shaped polymeric structure by ionizing radiation.

Other methods of altering the surface of polymeric objects include exposing the surface of a polymeric article to low temperature plasma or an electrically charged gaseous atmosphere, followed by contacting the surface of the polymeric article with a surface modifying compound as described, for example, in U.S. Pat. No. 4,344,981. This two-step method is generally called plasma-induced coating. Plasma induction has been described generally in U.S. Pat. No. 4,328,257, Yasuda, "Plasma for Modification of Polymers," *J. Macromol. Sci. C. Chem.*, a 10(3):383 (1978), Mittal, "Interfacial Chemistry and Adhesion: Recent Developments and Prospects," *Pure & Appl. Chem.*, 52:1295 (1980), Akovali, G. and Hasirci, N., "Polymerization of Hexamethyldisiloxane by Plasma on Activated Charcoal: Investigation of Parameters," *J. Appl. Polymer Sci.*, 29:2617 (1984) and Liu, W. T. et al., "Polymethyl Methacrylate Resist Sensitivity Enhancement in X-Ray Lithography by *In Situ* Polymerization," *Appl. Phys. Lett.*, 44:973 (1984), for example.

Ionized vapor or plasma discharge is typically created in a vacuum chamber in which the object to be modified is placed. The plasma discharge conditions the surface by creating free radicals and/or ions. It is known, for example, that exposing the surface of an object to plasma discharge, such as an oxygen plasma, enhances the wettability or hydrophilicity of such a surface. However, such treatment is only temporary. U.S. Pat. Nos. 3,925,178; 3,944,709; 4,072,769; 4,096,315; 4,122,942; 4,123,308; 4,131,691; 4,137,365; 4,214,014 and 4,478,873 disclose examples of polymers whose surface characteristics have been modified by a plasma discharge.

Plasma discharge treatment may also be used to prepare an object for the attachment or grafting of a compound or material to the plasma discharge treated object. For example, a plasma discharge step may be used to condition the surface for grafting by creating free radicals to which a compound or material may be grafted. Such compounds or materials are generally called surface modifiers. Knight, P. M. et al., in "Surface Modification of Intraocular Lenses to Reduce Corneal Endothelial Damage," *Am. Intra-ocular Implants Soc. J.*, 5:123 (1979) disclose one example of a polymer object having a surface modifier attached thereto using gamma irradiation and radio frequency (RF) gas plasma treatment to generate free radicals on the surface of a PMMA intraocular lens followed by polymerizing hydrophilic monomers, in particular, HEMA and vinyl pyrrolidone, as a coating on the surface of the lens. While the coated surfaces exhibited enhanced hydrophilicity, the coated surfaces were not stable when boiled to sterilize them. Surface modification by gamma radiation followed by polymerization on the surface, on the other hand, remained intact through several hours of boiling. However, such coated PMMA surfaces were damaging to rabbit endothelial cells and surfaces coated with dissolvable coatings, such as polyvinyl acetate, were preferred.

Another example of a surface treated polymer is disclosed in U.S. Pat. No. 4,312,575. This patent discloses a soft, highly oxygen permeable, hydrophobic polymeric lens which has on its surface an ultra-thin, optically clear, permeable barrier coating which is the reaction product resulting from a glow discharge polymerization process conducted in a hydrocarbon or halogenated hydrocarbon gaseous atmosphere. While the plasma discharge process, itself, results in a hydrophilic surface, subsequent exposure to a glow discharge atmosphere of oxygen or ambient oxygen yields a still more hydrophilic surface.

U.S. Pat. No. 4,409,258 discloses a method for rendering contact lenses hydrophilic by bombarding the lens, which may be PMMA or silicone, with a positive ion beam generated by a plasma discharge, such as an oxygen plasma. The lens is thereafter hydrated, preferably at an elevated temperature.

Examples of surface treated polymeric lenses for use in humans are included in U.S. Pat. No. 3,880,818. This patent discloses a soft contact lens that is flexible and physiologically compatible, which is made by manufacturing a hard, inflexible prepolymer, such as a hard acrylic acid-type polymer, and reacting the inflexible prepolymer with an alcohol to esterify pendent carboxyl groups with alkyl groups, hydroxy alkyl groups or alkoxyalkyl groups, containing no more than eleven carbon atoms.

U.S. Pat. No. 4,143,949 discloses a discharge polymerization and coating process for making a hydrophilic contact lens from an oxygen permeable, hydrophobic polymer. The hydrophobic lens is placed in a glow discharge apparatus containing an atmosphere comprising a polymerizable organic monomer, such as hydroxyalkyl acrylate or methacrylate, glycidyl methacrylate, propylene oxide or N-vinyl-2-pyrrolidone, where the glow discharge is used to polymerize the monomer onto the surface of the contact lens.

Other examples of surface treated polymeric objects include U.S. Pat. Nos. 3,228,741; 3,925,178; 3,959,105; 3,985,697; 4,055,378; 4,277,595; 4,405,773; 4,430,458; 4,463,148; and 4,731,080. U.S. Pat. No. 4,731,080, for example, discloses a coated intraocular lens having a hydrophobic cross-linked vinyl-containing silicone polymer placed on the lens surface in solution.

It would be desirable to have a biocompatible, surface modified material and a method for producing the same, where the surface modification is substantially permanent, results in a smooth surface on the cellular level and where the surface modified material may be used, inter alia, as a prosthetic device in mammals.

BRIEF SUMMARY OF THE INVENTION

According to the present invention, a method of permanently modifying the surface of a substrate material so that the substrate material develops a microscopically smooth, biocompatible surface comprises covalently grafting at least a first biocompatible material having pendant terminal carboxylic acid or amine groups to the surface of the substrate material by radio frequency plasma-induced grafting. In addition, according to the present invention, a method of permanently modifying the surface of a substrate material further comprises cross-linking a second biocompatible material to the first biocompatible material grafted to the substrate material using a cross-linking agent.

In addition, the present invention is directed to a method of permanently modifying the surface of a substrate material so that the substrate material develops a microscopically smooth, biocompatible surface comprising covalently grafting a biocompatible, hydrophilic or hydrophobic material to the surface of the substrate material by radio frequency plasma-induced grafting.

Further, the present invention is directed to a prosthesis used in mammals comprising a polymer substrate or core and at least a first biocompatible material grafted to the polymer core by plasma induction.

In addition, a prosthesis used in mammals further comprises a polymer core, a first biocompatible material having pendant terminal carboxylic acid or amine groups covalently grafted to the polymer core by plasma induction and a second biocompatible material cross-linked to the grafted first biocompatible material by a cross-linking agent.

DETAILED DESCRIPTION OF PREFERRED EMBODIMENTS

Although the methods of preparation of the invention apply generally to the preparation of permanent surface modification of many different materials, the methods are described and exemplified below with specific examples using polymeric intraocular lenses as prostheses which may be used in mammals. It will be understood by one skilled in the art that the methods of the present invention may be used to prepare permanently modified surfaces of other substrate materials, such as those prosthetic materials identified above. Moreover, it will be apparent to one skilled in the art that the methods of the present invention readily lend themselves to the preparation of materials having modified or enhanced surface characteristics having other uses.

According to the present invention, a first biocompatible material having pendant terminal carboxylic acid or amine groups is covalently grafted to the surface of a substrate material by radio frequency plasma induction. Examples of substrate materials to which a biocompatible material may be grafted include polymers, such as silicone, polypropylene, polyester, polytetraflouroethylene, polyurethane, HEMA and PMMA.

Generally, the substrate material used in accordance with the present invention is chosen dependent upon its intended use. For example, PMMA and HEMA are two materials of choice for use in prosthetic devices intended for implantation or other application in mammals. However, in view of the present specification, one skilled in the art will appreciate that any organic polymer may be used as a substrate material, as well as certain ceramics and metals. Where an optically clear polymer for use in prosthetic devices for mammals is the substrate material, it is presently preferred that the polymer comprises PMMA.

The surface properties of the substrate material (viz: hydrophobic for PMMA, for example) are modified by grafting a first biocompatible material having pendant terminal carboxylic acid or amine groups to the surface thereof. Once the substrate material surface has been modified by covalently grafting the biocompatible material to the surface of the substrate material, the modified surface should have properties which are relatively nontoxic and nonirritating to living tissues. In addition, the modified surface should not adversely affect the desired properties of the remainder of the substrate material, such as structural integrity and optical clarity, among others. In addition, the modified surface should be microscopically smooth. As used herein, the term "microscopically smooth" shall mean that the surface of the modified substrate should be featureless upon examination at an enlargement of about 10,000 x. Further, the modified surface should be absent of crystallinity, cross-linked and thermally stable. Further, surface modification of a substrate material in accordance with the present invention should result in a substrate material which exhibits a reduced contact angle or wettability of the polymer surface of less than about 30° to about 50°.

Where the substrate material is intended for use in or as a prosthetic device, such as an intraocular lens, the surface modification of the present invention should not adversely affect the transparency or ocular acuity of the substrate material. Further, the first biocompatible material to be grafted to the substrate surface preferably comprises a material that is relatively easy to polymerize in a gas plasma environment. Such materials include unsaturated compounds or those compounds containing nitrogen, silicone or halogen. Materials that are relatively difficult to polymerize in a gas plasma environment include saturated compounds, cyclic compounds, compounds with a high molecular weight, such as proteins, and those compounds containing oxygen.

Preferably, the first biocompatible material having pendant terminal carboxylic acid or amine groups comprises ethylenediamine, polyacrylic acid, allylamine and/or diethylenetriamine. In one embodiment of the present invention where the substrate material is intended for use as an intraocular lens, it is presently preferred that the first biocompatible material comprises acrylic acid (which polymerizes to polyacrylic acid [PAA] under plasma treatment). One skilled in the art will appreciate, however, that other suitable biocompatible materials having the properties described above may be used in accordance with the present invention.

The first biocompatible material should be grafted to the substrate material in a relatively uniform thickness and texture along the surface of the substrate material. In addition, especially where it is desired to use the substrate material as a prosthetic lens, it is preferred that the first biocompatible material is present on the surface of the substrate material in a relatively small thickness to prevent interference with the optical clarity of the lens. More preferably, the first biocompatible material is present in a monomolecular layer. In one embodiment of the present invention, for example, a surface modified substrate comprises a first biocompatible material grafted to the surface of a substrate material with a biocompatible material thickness of about 100 A.

Grafting of the first biocompatible material according to the present invention is conducted using radio frequency plasma-induced grafting. Other methods of grafting, such as electronic or ultra-violet (UV) radiation are not suitable where it is desired (as it is here) to modify only the surface of the polymer material. For example, where a prosthetic lens, such as a contact lens or intraocular lens, is desired to be modified, modification should be confined to the surface of the lens to avoid affecting the optical properties of the lens. Radio frequency plasma-induced grafting according to the present invention avoids structural modification below the outer-most surface layer, and generally results in more desirable optical properties.

Such gas plasma-induced grafting may be conducted in a radio frequency gas plasma reactor capable of generating a frequency of about 1 MHz to about 40 MHz. The frequency generated by a typical commercial gas plasma reactor is about 13.56 MHz, although one skilled in the art will recognize that higher and lower frequencies may be used to graft the biocompatible material to the surface of the substrate material in a radio frequency gas plasma reactor, depending on the substrate material and biocompatible material used, the relative ease or difficulty in preparing the surface of the substrate material for grafting, the relative ease or difficulty of vaporizing or polymerizing the biocompatible material, among other factors.

The first step of radio frequency plasma treatment according to this invention is the removal or etching of material from the surface of the substrate material being bombarded by the plasma. This process cleans the substrate and produces active species on the surface so treated, such as ions and free radicals, which can be used for inducing a graft reaction.

Generally, the rate of material removal may be controlled relative to the rate of deposition of a graft polymer by the frequency of the gas plasma, the power of the gas plasma, the treatment time, the gas used in the plasma, the gas pressure/concentration, and the type of bond desired on the treated substrate material surface, depending on the particular substrate material.

Plasma-induced grafting of the first biocompatible material to the substrate material may be conducted in radio frequency plasma reactors known in the art. The Branson model 3003-1813 is one example of a suitable radio frequency gas plasma reactor which may be used to create a suitable gas plasma atmosphere in which a first biocompatible material having the properties described above may be vaporized and polymerized for grafting. One skilled in the art will appreciate, however, that other plasma reactors and apparatus may be used in accordance with the present invention.

Preferably, the ambient gas used in the radio frequency gas plasma-induced grafting is selected from the group consisting of nitrogen, ammonia and argon. More preferably, the gas used in the radio frequency gas plasma reaction is argon. Argon is an inert gas which creates active sites but does not produce new bonding when applied to a substrate surface in a RF gas plasma reactor. Oxygen, on the other hand, for example, tends to produce peroxides in such plasma-induced grafting reactions and is, therefore, generally less desired. One skilled in the art will understand, however, that other suitable gases may be used in the plasma reaction in accordance with the present invention.

Surface modification by plasma-induced grafting in accordance with the present invention essentially comprises two steps: (1) plasma treatment or preparation of the substrate surface; and (2) introduction of the monomer of the first biocompatible material into the plasma where the monomer becomes grafted to the substrate surface. As discussed above, the plasma treatment of the substrate surface breaks surface bonds, generating ions and free radicals at the surface of the substrate material, thus "activating" the surface. Introduction of the monomer into the radio frequency induced plasma causes the monomer to react with the substrate surface, polymerize and become grafted to the substrate surface.

The length of time the first biocompatible material in an induced plasma state should be allowed to react with the substrate material depends upon several factors, including the plasma or radiation power, the radio frequency, the flow concentration or pressure, the temperature and the desired thickness of the grafted material. Preferably, the radiation power is about 10 watts to about 200 watts, depending upon the biocompatible material. For example, where the biocompatible material comprises silazane, hexamethyldisiloxane, NVP (discussed below) or PAA, it is presently preferred that the radiation power is about 50 watts. Where the biocompatible layer material comprises HEMA (discussed below), it is presently preferred that the radiation power is about 10 watts to about 100 watts. In any event, the reactor power used and the duration such power is used should be low and/or short enough so as to not induce thermal circulation and melt the substrate material. For example, where the substrate material comprises PMMA, the reaction conditions (i.e., power and duration) should not increase the temperature of the substrate material above about 40°-45° C. One skilled in the art may readily determine, in view of the plasma reaction variables described above, the desired plasma radiation power to be used in accordance with the present invention.

The plasma reaction is preferably conducted for a period of time of about 1 minute to about 30 minutes. More preferably, the plasma reaction is allowed to occur for a period of time of about 1 minutes to about 30 minutes. The flow concentration or vapor pressure of the plasma reactants in the reactor chamber should be low enough so that the particular monomer of the biocompatible material vaporizes when introduced into the reactor. Preferably, the vapor pressure is about 0.1 torr to about 0.6 torr. More preferably, the vapor pressure is about 0.4 torr.

The temperature in the plasma reaction should not be allowed to approach those temperatures which may damage the substrate material or the biocompatible material. High radiation power and any polymerization reaction (i.e., polymerization which may occur when the grafting reaction occurs; e.g.: polymerization to polyacrylic acid) tend to increase the temperature of the plasma reaction. It is desirable, therefore, to maintain the temperature in the plasma reaction below the temperature at which the substrate material and/or the graft material will be damaged, typically below about 40°-50° C.

In view of this disclosure, one skilled in the art may readily determine the reactants, time, pressure and temperature conditions for a reaction using given materials without undue experimentation. For example, in one embodiment of the present invention, liquid acrylic acid liquid is introduced into a plasma reactor chamber having a plasma-etched or treated body of PMMA where, because of the low pressure within the chamber, the acrylic acid vaporizes. The acrylic acid is exposed to 50 watts of radio frequency radiation at about 27.5° C. at a reactant or vapor pressure of about 0.4 torr.

In addition to the first biocompatible materials discussed above, it may be desired to use other materials which do not have pendant terminal carboxylic acid or amine groups but which exhibit good biocompatibility and exhibit the desired characteristics described above for the first biocompatible materials (i.e., not adversely affecting substrate, relatively easy to polymerize, etc.). Examples of such biocompatible materials include the hydrophobic materials hexamethyldisiloxane, silazane, and/or N-vinyl pyrrolidone (NVP) and the hydrophilic material HEMA, although one skilled in the art will recognize that other materials having the desired properties discussed above may be used in accordance with this invention. The method and materials for grafting such other biocompatible materials to a substrate material are the same as those radio frequency plasma-induced grafting methods and materials described above. However, where biocompatible materials which do not have pendant carboxylic acid or amine groups are used in accordance with this invention, further surface modification by cross-linking a second biocompatible material to the grafted material (discussed below) is unavailable.

Although not necessary, it may be desired in accordance with the present invention to further modify the surface of a substrate material by cross-linking a second biocompatible material to the grafted first biocompatible material. One skilled in the art will recognize, for example, that where PAA is grafted to the surface of a substrate material, pendant terminal carboxylic acid groups are available to react, particularly via a cross-linking agent, with a second biocompatible material. Where the grafted first biocompatible material comprises ethylenediamine or allylamine, for example, pendant amine groups are available to react with a second biocompatible material.

The post-plasma cross-linking of a second biocompatible material to the grafted first biocompatible material preferably occurs in a buffered solution where the cross-linking reaction may occur for several minutes to several hours and typically about 24 hours. Preferably, the buffer solution comprises an aqueous solution of sodium bicarbonate or acetic acid having a pH of about 3.

The second biocompatible material should be reactive with the cross-linking agent and, depending upon the intended use of the substrate material, should be chemically stable, nontoxic and non-irritating.

Preferably, the second biocompatible material comprises a polysaccharide, such as hyaluronic acid, hyaluronate, heparin, agarose or chondroitin sulfate. It is presently preferred that the second biocompatible material comprises chondroitin sulfate. One skilled in the art will recognize, however, that the second biocompatible material may comprise other chemicals and drugs, which may be cross-linked to the grafted first biocompatible material using a cross-linking agent in accordance with the present invention. It is believed that examples of suitable chemicals or drugs include methotrexate and other antimetabolic agents and immunosuppressors.

The cross-linking agent must be capable of attaching (cross-linking) the second biocompatible material to the pendant amine or carboxylic acid groups on the grafted first biocompatible material and must be incorporated into the first and second biocompatible cross-linked materials. The cross-linking agent, especially once incorporated into the cross-linked first and second biocompatible materials, should not adversely affect the biocompatibility of the modified surface of the substrate material and should not adversely affect the characteristics of the substrate material, the grafted first biocompatible material or the cross-linked second biocompatible material. Preferable cross-linking agents in accordance with the present invention include glutaraldehyde, bis(3,5-dibromosalicyl)fumarate, 1-ethyl-3-(3-dimethylaminopropyl)-carbodiimide (EDC) and carbodiimide In one embodiment of the present invention, the surface modified substrate material (i.e., the substrate material having a first biocompatible material grafted thereto), the cross-linking agent and the second biocompatible material are combined in a neutral buffer solution (pH about 7), where cross-linking to the surface modified substrate can occur.

In another embodiment of the present invention, the cross-linking agent and the second biocompatible material are mixed together prior to the addition of the surface modified substrate in a buffer solution, such as those buffer solutions described above.

Where it is desired to further modify the surface of a substrate by cross-linking a second biocompatible material to the grafted material in accordance with the present invention, the substrate having its surface modified by plasma-induced grafting should be relatively free from any excess reagents used during the grafting process. Generally, excess reagents may be removed by rinsing the surface modified substrate in distilled water.

Where the first biocompatible material is hydrophilic, the surface modified substrate material should exhibit a greater hydrophilicity than the untreated substrate material. Hydrophilicity may be measured by wettability or contact angle. Wettability or surface energy is related to surface tension and is measured in dyne/cm, which is easily conducted by submerging a testing surface into a solvent and removing the testing surface from the solvent. The more and faster the solvent beads up on the surface of the substrate, as determined by the diameter and volume of the beads or drops, the higher the wettability value.

The contact angle of a substrate is that angle formed when a drop of liquid is placed on the surface of the substrate and may be measured with a goniometer. Where the intended use of the substrate is in an aqueous environment, water is the preferred liquid. If the drop of liquid on the surface of the substrate is relatively flat, the substrate may be said to be hydrophilic and the contact angle is relatively low (i.e., about 5°–30°). Conversely, if the liquid drop is relatively beadlike, the substrate may be said to be less hydrophilic and has a relatively higher contact angle (i.e., about 70°–110°). For example, the contact angle of untreated PMMA is about 77°. The contact angle of PMMA treated in accordance with the present invention with: (1) an argon gas plasma is about 45° to about 65°; (2) a polyacrylic acid graft is about 45° to about 55°; (3) oxygen gas plasma treatment subsequent to grafting is about 30° to about 55°; (4) an allylamine graft is about 30° to about 40°; and (5) CDS cross-linked to the PAA graft is about 10° to about 15°. Preferably, the contact angle of a material for use in or as a prosthetic device is about 45° or less and more preferably, about 15° or less.

Novel products having a permanently modified surface resulting from the method of the present invention described above include prostheses for use in mammals comprising a polymer substrate or core and a biocompatible material grafted thereto. For example, one presently preferred prosthesis for use in mammals comprises a PMMA core having a modified surface comprising PAA substantially permanently grafted to the PMMA surface.

In addition, novel products having a permanently modified surface using the method of the present invention include prostheses used in mammals comprising a polymer core, a first biocompatible material grafted thereto and a second biocompatible material cross-linked to the grafted coating by a cross-linking agent. In one embodiment of the present invention, for example, a prosthesis used in mammals comprises a PMMA core, having a modified surface comprising PAA grafted to the PMMA surface and chondroitin sulfate cross-linked to the PAA using glutaraldehyde as the cross-linking agent.

Other novel products produced using the method of the present invention include an intraocular lens having a permanently modified, biocompatible surface, which comprises a polymer lens body, such as PMMA, a first biocompatible material having pendant carboxylic acid or amine groups, such as PAA or ethylenediamine grafted to the surface of the lens body, and a second biocompatible material, such as chondroitin sulfate cross-linked to the grafted first biocompatible material via a cross-linking agent, such as glutaraldehyde.

The invention will now be illustrated in further detail by reference to the following specific, non-limiting examples.

EXAMPLE 1

An intraocular lens manufactured by CILCO (J-FLEX posterior chamber lens style SK-1) from PMMA was positioned in a Branson model 3003-1813 radio frequency gas plasma reactor. The pressure inside the reactor was reduced to less than about 0.10 torr and the surface of the lens was subjected to an argon gas (Ar) plasma at approximately 40° C. at 50 watts for 3 minutes. Acrylic acid vapor was introduced into the reactor and was allowed to react for 5 minutes at about 0.3 torr. Upon examination, the lens exhibited a uniform surface with a smooth texture and good biocompatibility in animal testing (no cellular or tissue remnant adhesion) with a contact angle of about 50°.

EXAMPLE 2

The procedures of Example 1 were followed, substituting ethylenediamine (EDAM) for acrylic acid. The resulting lens coating had a contact angle of 35°–45° and exhibited a smooth microstructure upon SEM analysis.

EXAMPLE 3

The coated lens prepared in Example 2 was placed in a vessel containing 2ml (25% solution) glutaraldehyde, 1.5 g chondroitin sulfate, 1 ml (25% solution) polyacrylic acid and acetic acid sufficient to adjust pH to about 3 (3-4ml). The mixture was brought to 100 ml by addition of distilled water. The mixture was allowed to incubate at room temperature for 24 hours, rinsed with distilled water and dried. Scanning electron micrograph examination of the lens indicated that the surface had a thick film having a very coarse texture. The water contact angle was less than about 10°–15°, indicating that chondroitin sulfate had attached to the surface. The dry lens had a hazy appearance which disappeared upon immersion in water. Lens clarity and acuity was not significantly altered, as confirmed by spectroscopic measurements.

EXAMPLE 4

Following the procedures of Example 3 a series of intraocular lenses were treated. Table 1 indicates the steps and/or materials used or present (indicated by a "Y") for each run and the resulting contact angles for each lens.

TABLE 1

| Run | Ar | EDAM | Buffer (8.4) | PAA | GDA (.5%) | CDS/GDA (.05%) | CDS/GDA (.1%) | Rinse (4° C.) | Contact Angle (F/A) |
|---|---|---|---|---|---|---|---|---|---|
| 1 | Y | Y | Y | Y | Y | Y |   | Y | 39/44 |
| 2 | Y | Y | Y | Y | Y |   | Y | Y | 31/35 |
| 3 | Y | Y | Y |   | Y | Y |   | Y | 42/53 |
| 4 | Y | Y | Y |   | Y |   | Y | Y | 42/51 |
| 5 | Y | Y | Y/3 |   | Y | Y |   | Y | 35/40 |

F = freshly prepared lens
A = aged lens
Y = present or conducted

EXAMPLE 5

An intraocular lens manufactured by CILCO from PMMA as in Example 1 was placed in a Branson model 3003-1813 radio frequency gas plasma reactor. The pressure within the reactor was reduced to about 0.1 torr and an argon gas plasma was created using about 50 watts radio frequency at 40° C. The plasma reaction was allowed to proceed for about 5 minutes. The contact angle of the non-treated PMMA intraocular lens was about 70. and the contact angle of the argon plasma treated lens was about 45°. The lens was put back in the reactor and vapor acrylic acid was introduced into the chamber. The pressure was reduced to about 0.3 torr and a portion of the acrylic acid was ionized using 50 watts. The plasma reaction was allowed to continue for 5 minutes. The contact angle of the acrylic acid modified surface (polyacrylic acid graft) treated lens was about 35°. The lens was placed back into the reactor and treated with an oxygen gas plasma using 50 watts at about 0.2 torr for 1–3 minutes. The contact angle of the lens after oxygen plasma treatment was about 30°.

EXAMPLE 6

The lens prepared in Example 5 was placed in a sodium bicarbonate buffer solution to which was added 9mg EDC and allowed to react for 120 minutes at 37° C. In a second vessel, 1.5 g chondroitin sulfate and 0.1 g EDC were mixed in distilled water for 120 minutes at 37° C. The chondroitin sulfate/EDC mixture was added to the lens solution and allowed to react for 24 hours.

The present invention may be embodied in other specific forms without departing from the spirit or essential attributes thereof and, accordingly, reference should be made to the appended claims, rather than the specification, as indicating the scope of the invention.

We claim:

1. A method of permanently modifying the surface of a substrate material to produce a microscopically smooth, biocompatible surface thereon, comprising covalently grafting a polymeric, first biocompatible material to the surface of the substrate material by radio frequency plasma induction, the biocompatible material having pendant terminal carboxylic acid or amine groups.

2. The method according to claim 1, wherein the grafting is induced in a radio frequency plasma reactor generating a frequency of about 1 MHz to about 40 MHz.

3. The method according to claim 2, wherein the frequency is about 13.56 MHz.

4. The method according to claim 2, wherein gas is present in the reactor, said gas being selected from the group consisting of nitrogen, ammonia and argon.

5. The method according to claim 4, wherein the gas is argon.

6. The method according to claim 1, wherein the first biocompatible material comprises ethylenediamine, polyacrylic acid, diethylenetriamine or allylamine.

7. The method according to claim 1, wherein the substrate material is selected from the group consisting of silicone, polypropylene, polyester, polytetrafluoroethylene, polyurethane, hydroxyethylmethacrylate and polymethyl-methacrylate.

8. The method according to claim 1, lo wherein the surface of the substrate material is further modified by covalently cross-linking a second biocompatible material to the grafted first biocompatible material using a cross-linking agent.

9. The method according to claim 8, wherein the cross-linking agent is applied to the substrate material surface prior to the application of the second biocompatible material.

10. The method according to claim 8, wherein the second biocompatible material comprises a polysaccharide.

11. The method according to claim 10, wherein the polysaccharide is selected from the group consisting of hyaluronic acid, hyaluronate, agarose and chondroitin sulfate.

12. The method according to claim 10, wherein the polysaccharide is chrondroitin sulfate.

13. The method according to claim 8, wherein the cross-linking agent is selected from the group consisting of glutaraldehyde, bis(3,5-dibromosalicyl)fumarate, 1-ethyl-3-(3-dimethylaminopropyl)-carbodiimide and carbodiimide.

14. The method according to claim 8, wherein the cross-linking agent is glutaraldehyde.

15. The method according to claim 8, wherein the substrate material is rinsed with distilled water prior to cross-linking the second biocompatible material to the grafted first biocompatible material.

16. The method according to claim 8, wherein the cross-linking occurs in the presence of a neutral buffer solution.

17. The method according to claim 1, wherein said first biocompatible material is polyacrylic acid, said substrate is a polymethylmethacrylate substrate, said grafting is induced by argon gas plasma at a frequency of about 13.56 MHz, and after said grafting, said substrate is rinsed with distilled water, and glutaraldehyde and chondroitin sulfate are applied sequentially in a neutral buffer solution to said polyacrylic acid grafted to said polymethylmethacrylate substrate.

18. The method according to claim 1, wherein, prior to radio frequency plasma induction, the first biocompatible material is a monomer.

19. The method according to claim 18, wherein the monomer of the first biocompatible material is selected from the group consisting of the monomers of ethylenediamine, polyacrylic acid, diethylenetriamine and allylamine.

20. A method of permanently modifying the surface of a substrate material to produce a microscopically smooth, biocompatible surface thereon, comprising covalently grafting a biocompatible, hydrophilic polymeric material to the surface of the substrate material by radio frequency plasma induction.

21. The method according to claim 20, wherein the biocompatible, hydrophilic polymeric material comprises ethylenediamine, polyacrylic acid, hydroxyethylmethacrylate, diethylenetriamine or allylamine.

22. A method of permanently modifying the surface of a substrate material to produce a microscopically smooth, biocompatible surface thereon, comprising covalently grafting a biocompatible, hydrophobic polymeric material to the surface of the substrate material by radio frequency plasma induction.

23. The method according to claim 22, wherein the biocompatible, hydrophobic material comprises N-vinylpyrrolidone, silazane and hexamethyldisiloxane.

* * * * *